United States Patent [19]

Bell

[11] Patent Number: 5,040,676

[45] Date of Patent: Aug. 20, 1991

[54] CONTAINER AND DISPENSER FOR AN ANEURYSM CLIP

[75] Inventor: Richard L. Bell, Marshfield, Mass.

[73] Assignee: Codman & Shurtleff, Inc., Randolph, Mass.

[21] Appl. No.: 546,488

[22] Filed: Jun. 29, 1990

[51] Int. Cl.⁵ .............................................. B65D 85/00
[52] U.S. Cl. .................................................... 206/339
[58] Field of Search ......................................... 206/339

[56] References Cited

U.S. PATENT DOCUMENTS 4,938,353  7/1990  Bell ...................................... 206/339

Primary Examiner—William I. Price

[57] ABSTRACT

A container and dispenser for an aneurysm clip adapted to receive many different sizes of aneurysm clips and to hold them in a position which facilitates easy removal of the clip from the container. The holder has a generally rectangular body, a detent projecting from its bottom surface and a platform extending from its front surface. the front surface also includes a recess in which is placed a number of projections for supporting various size aneurysm clips.

8 Claims, 5 Drawing Sheets

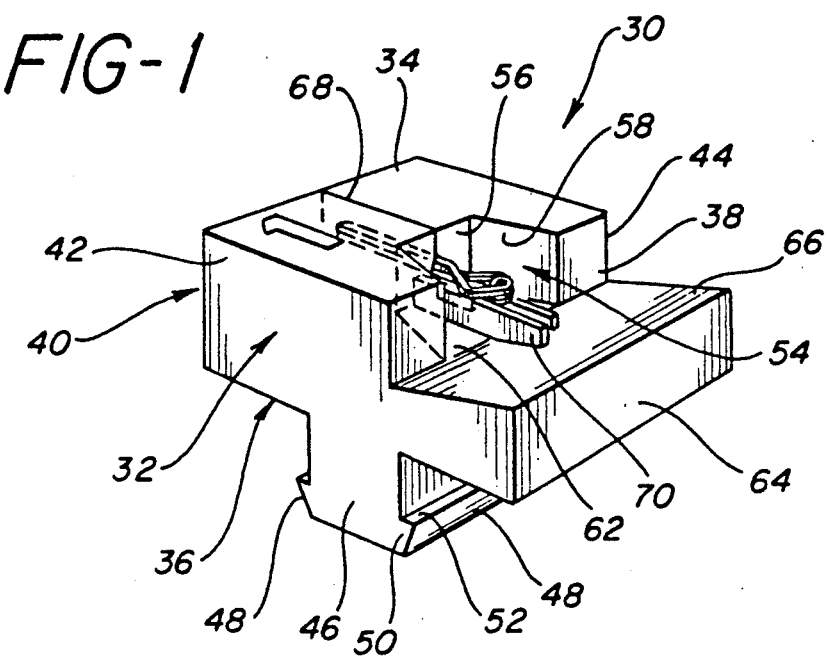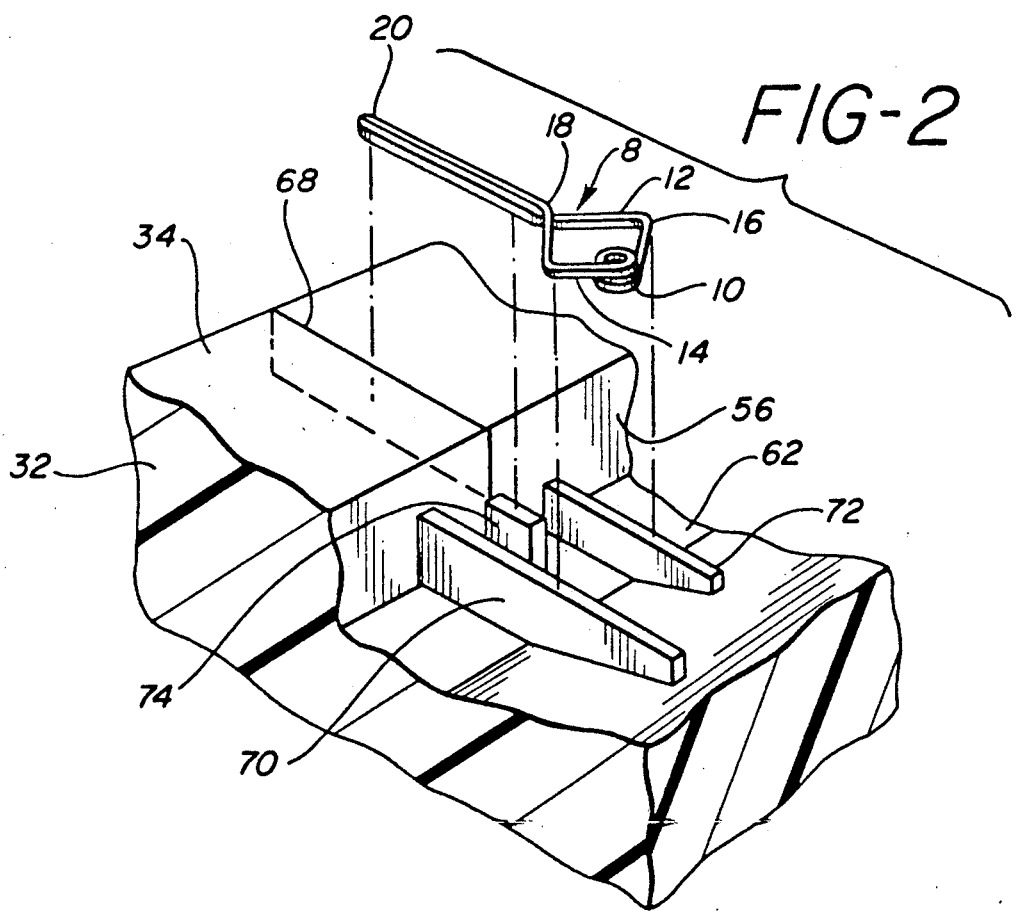

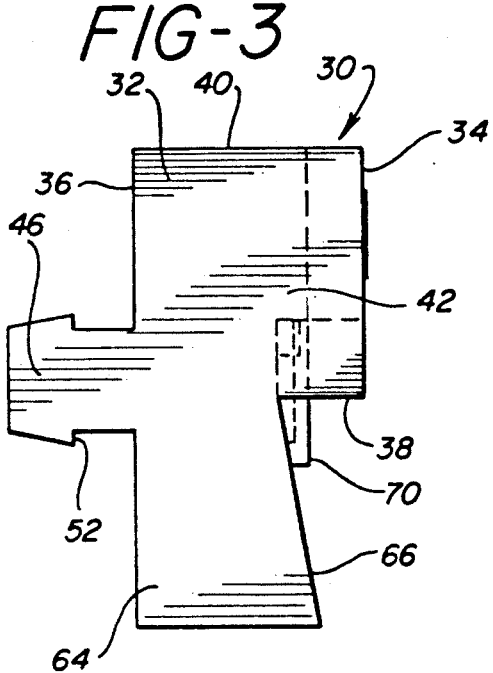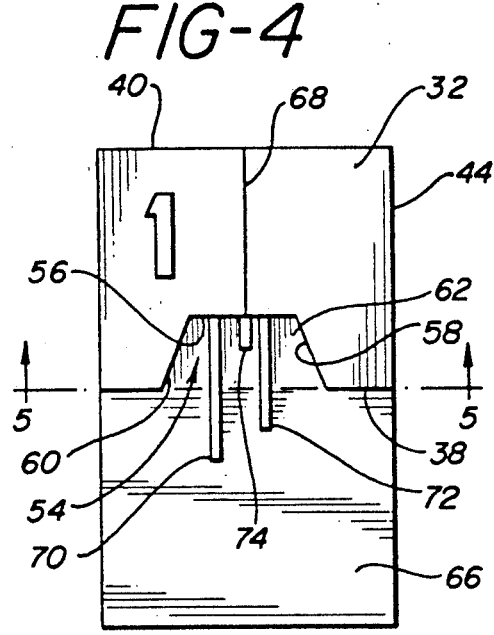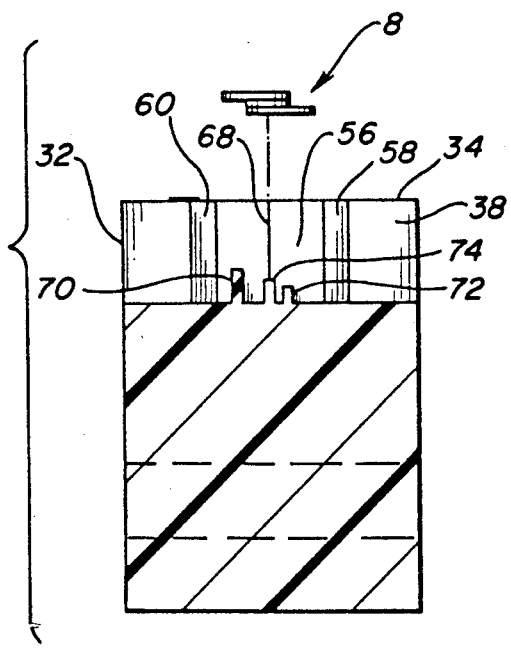

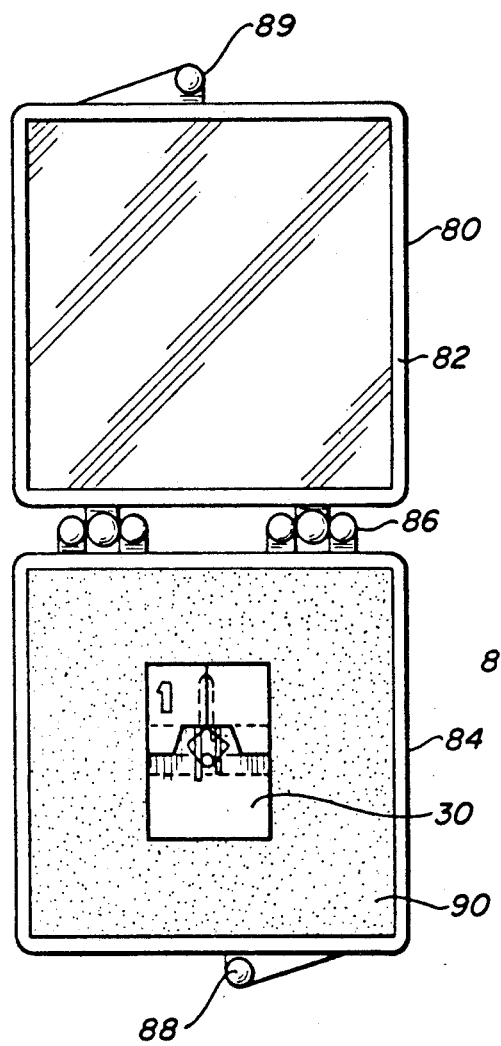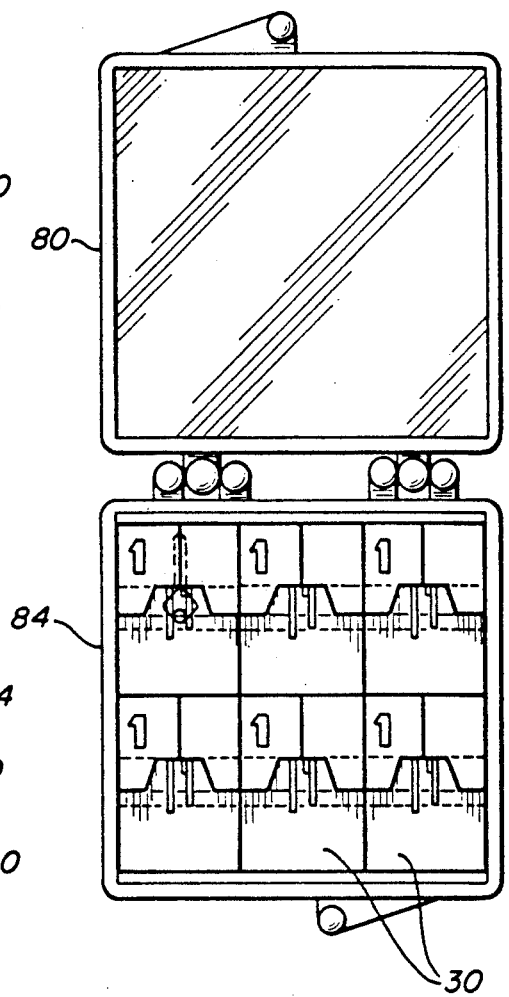

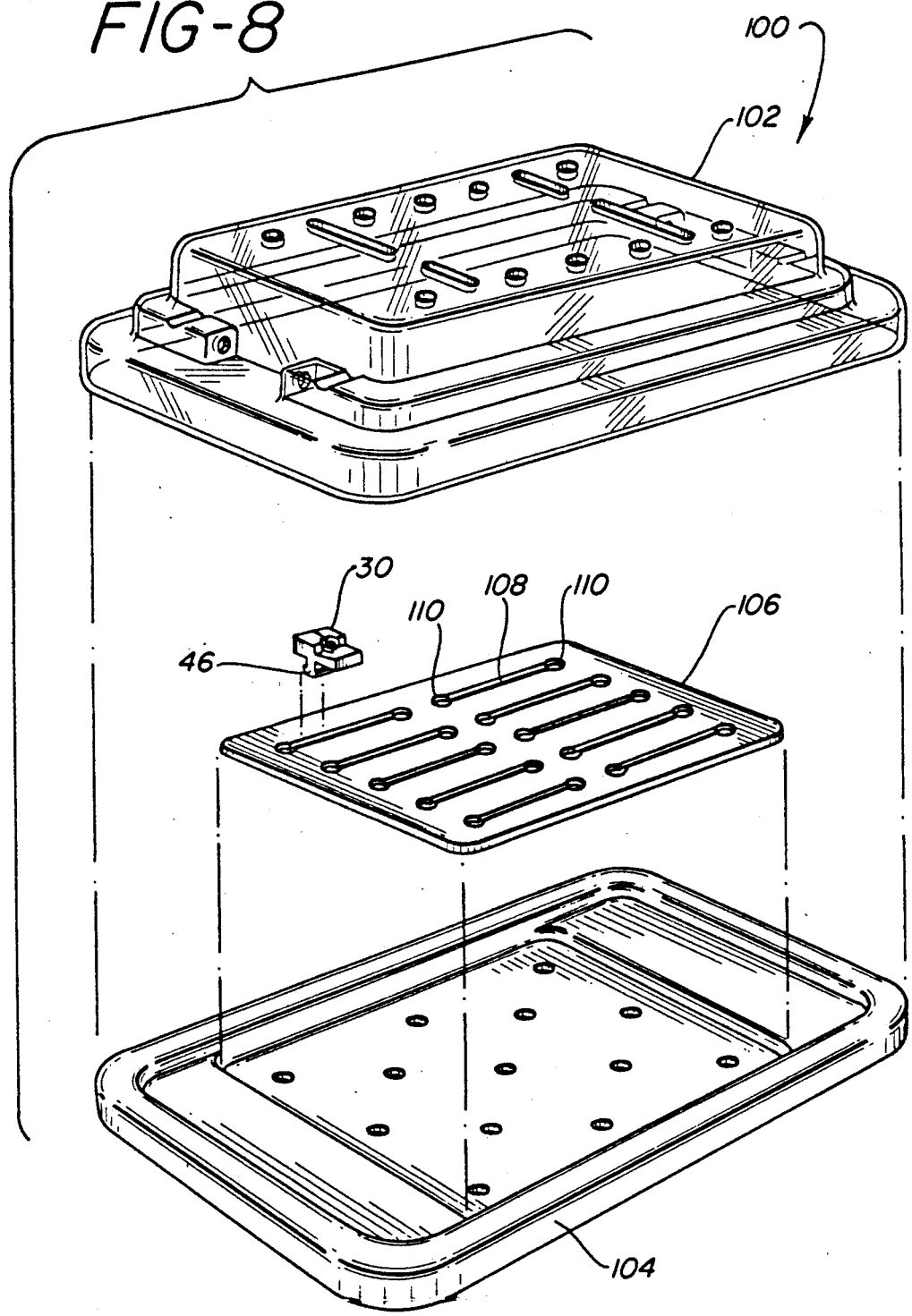

5,040,676

CONTAINER AND DISPENSER FOR AN ANEURYSM CLIP

The present invention relates to a container and dispenser for an aneurysm clip and, more particularly, to a container which will receive a variety of sizes of aneurysm clips.

BACKGROUND OF THE INVENTION

An aneurysm clip 8 of the kind stored in the container and dispenser of the present invention is shown for example, in U.S. Pat. No. 3,827,438 and is shown generally in FIG. 2 of the disclosure of this patent application. The disclosure of U.S. Pat. No. 3,827,438 as it relates to aneurysm clips is incorporated into this application by reference. This kind of clip 8 has a torsion spring coil 10 with a first arm 12 extending from one end of coil 10 and a second arm 14 extending from the other end of coil 10. Each of the first and second arms 12 and 14 has a shoulder portion 16, a cross over portion 18 and jaws 20. When the shoulder portions are moved together (with a special forceps, not shown), jaw portions 20 move away from each other toward the open position so that an aneurysm can be grasped between the two confronting jaw portions.

Certain aneurysm clips are very small. Their small size makes them difficult to grasp properly in a special forceps called an aneurysm clip applier. It would be desirable to have a container and dispenser for aneurysm clips, particularly very small aneurysm clips, to make it easier for the user to properly grasp the clip. It would also be desirable to have one dispenser that would accommodate various size clips.

SUMMARY OF THE INVENTION

The present invention provides a holder and dispenser for an aneurysm clip which includes a generally rectangular body, a recess in the front surface of the body, at least two spaced apart projections located at least partially within the recess, extending along the base of the recess and raised above the recess for supporting a coil type aneurysm clip. As it will be noted in FIG. 2, the two arms 12 and 14 of a coil type aneurysm clip are at different heights because they extend from different ends of the coil. Thus, the projections which hold this clip are at different heights so that the clip will rest more or less flat on the projections.

The holder also includes a slit extending into the body from the recess rear wall from a position between the two projections. There may also be a third projection extending between the first two projections to allow the holder to support a still wider variety of aneurysm clips.

The holder also includes a platform extending from the front surface of the body and aligned generally with the base of the recess. The top surface of the platform may be angled down into the recess to help the user align an aneurysm clip applier to more easily grasp the aneurysm clip shoulders in the jaws of the applier.

The holder also has a retainer projecting from the bottom of the body. The retainer has detents for holding the body in corresponding slots in a sterilization tray.

The base is preferably made of a soft elastomeric material. One or more holders may be placed in a plastic container for shipment. If only one holder is used then that holder is mounted inside a foam insert within the case. Each holder is embossed with a number indicating the size of the clip that is held in the holder.

These and other features and advantages of the present invention will become more apparent from the following detailed description of the preferred embodiments taken in conjunction with the following drawings.

BRIEF DESCRIPTION OF THE DRAWINGS

FIG. 1 shows a perspective view of the holder of the present invention;

FIG. 2 shows a detailed perspective view, partially in section, of a portion of the holder shown in FIG. 1 with an aneurysm clip ready for placement in the holder;

FIG. 3 shows a side elevation of the holder of FIG. 1;

FIG. 4 shows a top plan view of the holder of FIG. 1;

FIG. 5 shows a front elevation, partially in section, taken along lines 5—5 in FIG. 4;

FIG. 6 shows a top plan view of a single holder in a case;

FIG. 7 shows a top plan view of several holders in a case;

FIG. 8 shows an exploded perspective view of a sterilization tray with a special insert in which holders are held for sterilization; and, FIG. 9 shows a partial top view partly in section of the sterilization tray and insert of FIG. 8 showing a variety of holders inserted in the insert.

DETAILED DESCRIPTION OF THE PREFERRED EMBODIMENT

Figure 9:
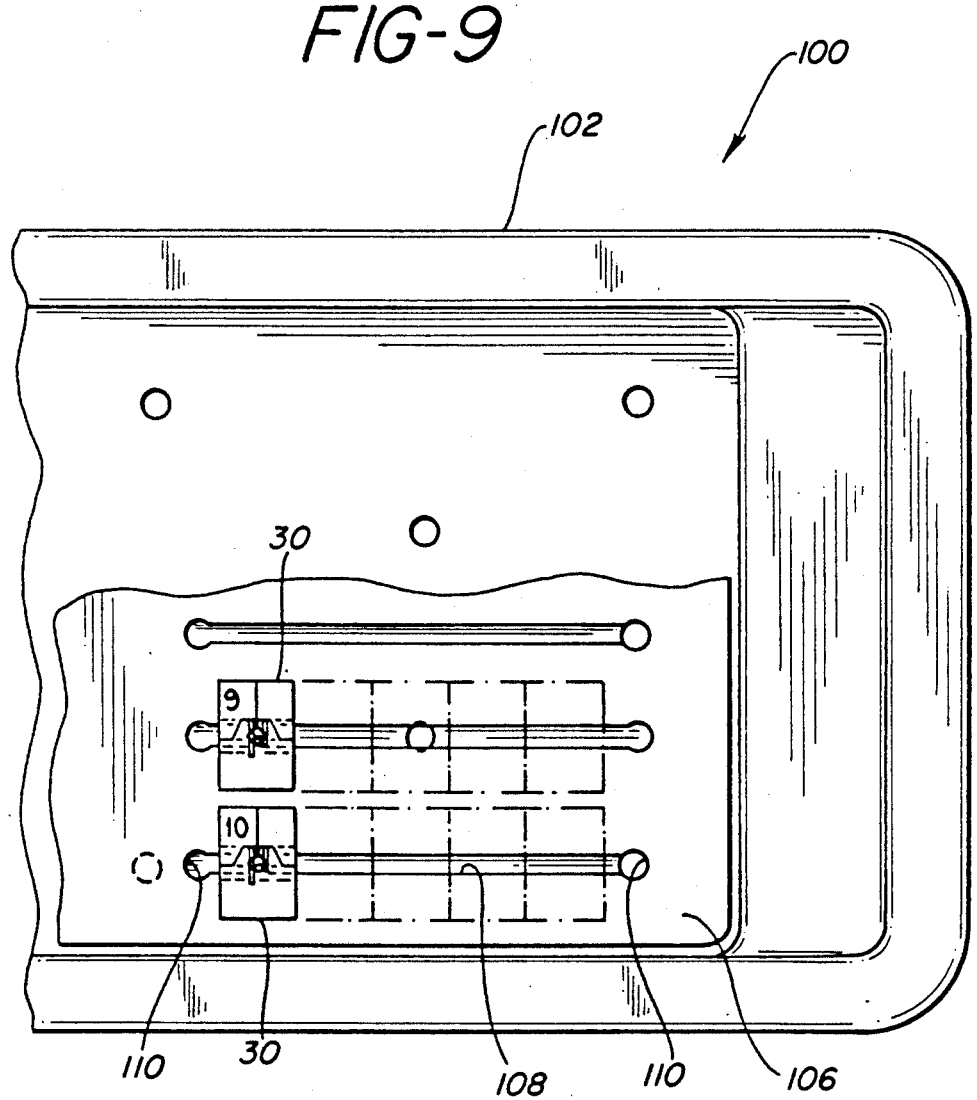

Referring now to FIG. 1 there is shown a perspective view of the holder 30 of the present invention including a generally rectangular body 32 having a top 34, bottom 36, front 38, back 40, left side 42 and right side 44. A retainer 46 projects from bottom 36 and includes detents 48 for holding holder 30 in sterilization tray insert 106 (see FIG. 8) to be described later in the application. Detent 48 includes a flange 50 cut at an angle to define a shelf 52.

Front surface 38 of body 32 includes a recess 54 having a rear wall 56, side walls 58 and 60, base 62 and an open top.

Platform 64 projects from front surface 38 of body 32 and includes a top surface 66 which blends into recess base 62. Top surface 66 of platform 64 preferably, but not necessarily, forms an angle of about 10° with recess base 62.

Body portion 32 has a slit 68 extending from rear wall 56 of recess 54 into body portion 32 and preferably through body portion 32 all the way to back surface 40. This slit 68 accommodates jaws 20 of aneurysm clip 8 to hold aneurysm clip 8 firmly in position.

Holder 30 is made of an elastomeric material such as silicone, urethane or styrene and is most preferably made of styrene butadiene styrene. Slit 68 in body portion 32 is formed by cutting body portion 32 with a sharp knife. Slit 68 has a transverse dimension in the vicinity of 0.004 inches.

Projections 70 and 72 extend from rear wall 56 of recess 54 along recess base 62 and on to top surface 66 of platform 64. The height of projection 70 above base 62 is greater than the height of projection 72 above recess base 62 to accommodate the difference in height between the arms 12 and 14 of a coil type aneurysm clip 8. The length of projections 70 and 72 in a direction extending away from rear wall 56 are different in order to accommodate a variety of clip sizes with one set of projections. A further variety of clips may be accommodated by holder 30 by including a third projection 74 which has a height less than the height of projection 70 but greater than the height of projection 72. Third projection 74 extends for a distance from wall 56 less than the distance that either projections 70 or 72 extend from wall 56. The use of third projection 74 permits a larger variety of sizes of clips to be held by holder 30. The specific dimensions and relative dimensions of projections 70, 72 and 74 have been described in accord with the preferred embodiment of holder 30. However, various dimensions and relative dimensions could be used so long as clip 8 is held in proper position to facilitate grasping with an aneurysm clip applier (not shown).

One will note, particularly from FIGS. 4 and 5, that slit 68 is aligned to the right side of projection 74 and generally between projections 70 and 72. The precise placement of slit 68 with respect to projections 70, 72 and 74 is not critical and any convenient position may be chosen so long as clip 8 is firmly held in position.

One will note in FIGS. 1 and 4 that a numeral appears in top surface 34 of body 30. This numeral indicates the size of the clip held in body 30. Different numbers may be used to identify different clips as is shown particularly in FIG. 9 where the numerals 9 and 10 are shown in the holders in FIG. 9.

One will note, particularly from FIG. 3 but also from FIGS. 1 and 2, that top surface 66 of platform 74 is arranged at an angle of about 10° to recess base 62. This angle helps the surgeon orient clip applier forceps when attempting to grasp clip 8 out of holder 30.

One will also note that the side walls 58 and 60 of recess 54 are flared outwardly to provide sufficient space for the jaws of an aneurysm clip applier (not shown) to readily be inserted into recess 54 to grasp clip 8.

Referring now to FIG. 6, there is shown a case 80 having a top 82 and bottom 84 connected by hinge 86 and having a snap clasp 88, 89. This case is conventional and is not part of this invention. In FIG. 6, bottom 84 holds a foam insert 90 with a central opening therein (not shown) into which a single holder 30 may be inserted and securely held.

Referring now to FIG. 7, there is shown the same case 80, the bottom 84 of which houses six separate holders 30 all designated by embossed numeral "1" indicating that all holders hold the same size clip. Holders with different embossed numerals holding different size clips could be incorporated into the case 80 shown in FIG. 7.

Referring now to FIG. 8, there is shown a exploded perspective view of a conventional sterilization tray 100 having a conventional top 102 and a conventional bottom 104 with a special insert 106 designed to a hold a plurality of holders 30 for sterilization. Insert 106 has a plurality, preferably 10, of slot 108 extending completely therethrough with key holes 110 on each end of each slot 108 to facilitate the insertion of retainer 46 into slot 108. The thickness of insert 106 conforms to the distance between bottom surface 36 of body 32 and shelf 52 of retainer 46. The width of detent 48 is slightly larger than the width of slot 46 so that detent 48 will snap into and be held by slot 108. It will be appreciated that holders 30 and their respective clips 8 can be sterilized in a conventional manner in sterilization tray 100.

The present invention has been described in conjunction with preferred embodiments. Those skilled in the art will appreciate that many modifications and changes may be made to the preferred embodiments without departing from the present invention. It is, therefore, not intended to limit the present invention except as set forth in the appended claims.

I claim:

1. A holder for an aneurysm clip comprising:
   a generally rectangular body having top, bottom, front, back, and left and right side surfaces;
   a recess in said front surface having side walls, a rear wall, a base and an open top;
   at least two spaced apart projections located at least partially within said recess and extending along said recess base out of said recess for supporting an aneurysm clip, the height of each said projections above said base being different;
   a slit extending into said body from said recess rear wall and positioned between at least two projections.

2. The holder of claim 1 wherein said body is made of a flexible elastomeric material.

3. The holder of claim 1 wherein said holder is made of styrene butadiene styrene copolymer.

4. The holder of claim 1 adapted for a coil type aneurysm clip having a coil spring at its proximal end, jaws at its distal end and a cross over point between said distal and proximal end, said coil spring having an axis aligned perpendicular to the plane of movement of said jaws, a first shoulder emanating from one end of coil spring and connecting to one of said jaws, a second shoulder emanating from the other end of said coil spring and connecting to said other jaw; and wherein the height difference between said at least two projections is great enough to accommodate the difference in height between said first and second shoulders.

5. The holder of claim 1 further including a platform projecting from the front surface of said body, said platform having a top surface extending from the front surface of said body and aligned with the base of said recess.

6. The holder of claim 5 wherein said platform top surface slopes with respect to said recess base.

7. The holder of claim 1 further including a retainer projecting from said bottom surface of said body and having detents thereon for holding said body in a sterilization tray.

8. The holder of claim 1 wherein said recess base includes a third projection within said recess said third projection having a height above said recess base between the heights of said at least two projections for supporting a clip, said third projection extending along said recess base an amount less than that of either of said at least two projections.

* * * * *